United States Patent [19]

Jones

[11] 4,305,891
[45] Dec. 15, 1981

[54] METHOD FOR PREPARING O-4-(HYDROXYALKYL)-THIOPHENYL PHOSPHATES

[75] Inventor: Francis W. Jones, Highton, Australia

[73] Assignee: Commonwealth Scientific and Industrial Research Organization, Canberra, Australia

[21] Appl. No.: 140,115

[22] Filed: Apr. 14, 1980

[30] Foreign Application Priority Data

Apr. 20, 1979 [AU] Australia .................. PD8478

[51] Int. Cl.³ .................. C07F 9/165; C07F 9/09
[52] U.S. Cl. .................. 260/968; 260/949
[58] Field of Search .................. 260/949, 973, 968

[56] References Cited

U.S. PATENT DOCUMENTS 3,792,132  2/1974  Bernhart .................. 260/949 X

OTHER PUBLICATIONS

Wagner et al., "Synthetic Organic Chemistry," (1953), pp. 169–170.

*Primary Examiner*—Anton H. Sutto
*Attorney, Agent, or Firm*—Norbert P. Holler; James J. Long

[57] ABSTRACT

Organophosphorus esters, useful as intermediates in the synthesis of fibre-reactive insect proofing agents for keratinous materials, are prepared as follows:

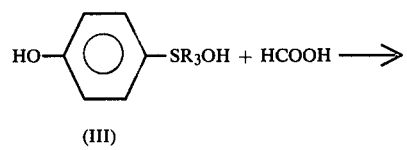

(III)

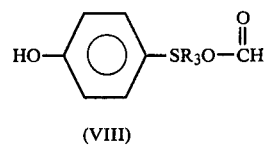

(VIII)

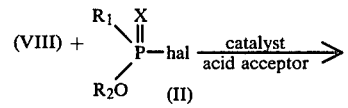

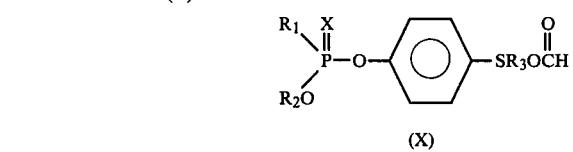

(X)

(X) + H₂O $\xrightarrow{\text{alkaline pH}}$

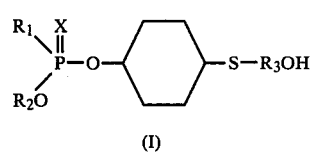
(I)

wherein:
$R_1$ is an alkyl, alkoxy, alkylamino or alkylmercapto radical with 1–6 carbon atoms a dialkylamino radical of 2 to 6 carbon atoms or a phenyl or amino radical;
$R_2$ is an alkyl radical of 1–6 carbon atoms;
$R_3$ is a divalent alkylene radical of 1–12 carbon atoms;
X is either a sulphur or oxygen atom; and
hal is either a chlorine or bromine atom.

20 Claims, No Drawings

METHOD FOR PREPARING O-4-(HYDROXYALKYL)-THIOPHENYL PHOSPHATES

This invention relates to a method making certain organophosphorus esters.

More particularly, the invention relates to a process for the production of 0-4-(hydroxyalkyl)thiophenyl-organophosphorus esters represented by formula (I):

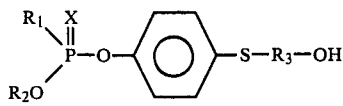

where
- $R_1$ is an alkyl, alkoxy, alkylamino, or alkylmercapto radical with 1-6 carbon atoms or a dialkylamino radical of 2-6 carbon atoms, a phenyl or amino radical,
- $R_2$ is an alkyl radical with 1-6 carbon atoms,
- $R_3$ is a divalent alkylene radical with 1-12 carbon atoms and
- X is either a sulphur or oxygen atom.

Such compounds represented by formula (I) are useful as intermediates in the preparation of fibre-reactive insect proofing agents for keratinous materials, in which case preferably:
- $R_1$ is an alkoxy or alkylmercapto radical of 2-4 carbon atoms and most preferably is an ethoxy or n-propylmercapto radical,
- $R_2$ is preferably a straight chain alkyl radical of 1-3 carbon atoms and most preferably is an ethyl radical and X is preferably a sulphur atom.

As described in Australian Patent Application No. 39575/78 the compounds of formula (I) have been obtained by the following reaction sequences:

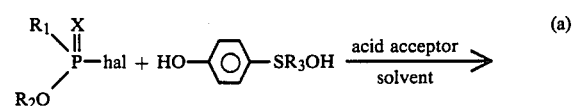

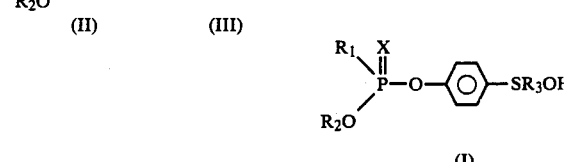

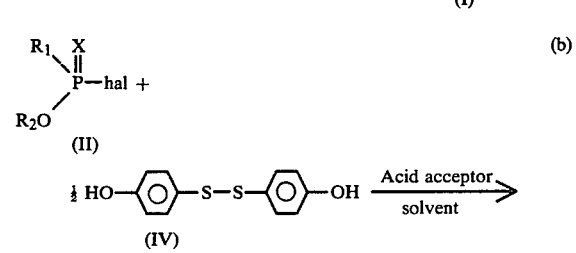

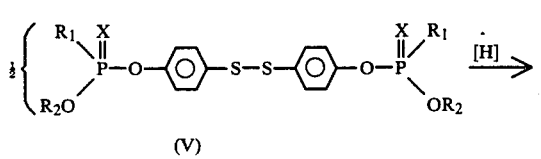

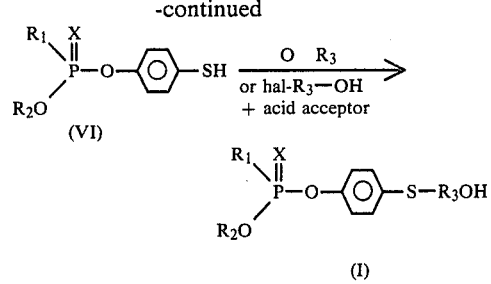

where $R_1$, $R_2$, $R_3$ and X have the above meaning and hal is a bromine or chlorine radical.

The prior art reaction sequence (a) is difficult to control and, on a large scale, significant amounts of the undesirable bis-phosphorylated product (VII) is formed:

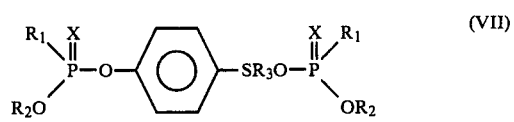

These products cannot be readily separated except by liquid chromatography.

The prior art reaction sequence (b) avoids the formation of (VII) but involves the reduction of (V) to (VI). The reducing agents most suitable for performing this reduction are phosphines which are relatively expensive. The use of cheaper reducing agents produces much lower yields.

The invention seeks to provide a method of producing the compound of formula (I) which may utilize cheaper reagents and produce higher yields than the prior art methods. Further, the production of undesirable contaminants may be reduced or eliminated.

According to the present invention there is provided a method for the preparation of 0-4-(hydroxyalkyl)-thiophenyl) organophosphorus esters of the formula (I):

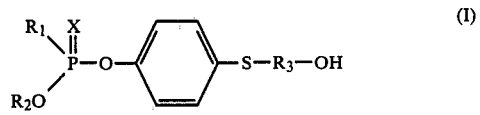

wherein the phenolichydroxyl group of a compound of formula (VIII):

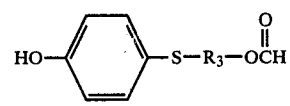

is phosphorylated by reaction with a compound of the formula:

in the presence of an acid acceptor to form a compound of the formula:

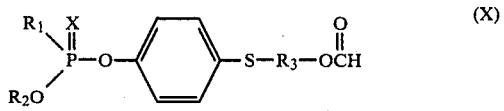

and the formyl ester group is removed from the compound of formula (X) by reaction in an alkaline solution where $R_1$ is an alkyl, alkoxy, alkylamino or alkylmercapto radical with 1–6 carbon atoms a dialkylamino radical of 2 to 6 carbon atoms or a phenyl or amino radical;

$R_2$ is an alkyl radical of 1–6 carbon atoms;

$R_3$ is a divalent alkylene radical of 1–12 carbon atoms;

X is either a sulphur or oxygen atom; and hal is either a chlorine or bromine atom.

Preferably, the compound of the formula (VIII) is prepared by formylation of the alcoholic hydroxyl group of a 4-(hydroxyalkyl)thiophenyl of the formula (III):

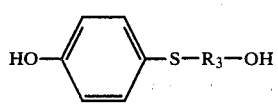

wherein $R_3$ is as defined above.

The preferred synthesis of compounds of formula (I) in the present invention is carried out by the reaction sequence:

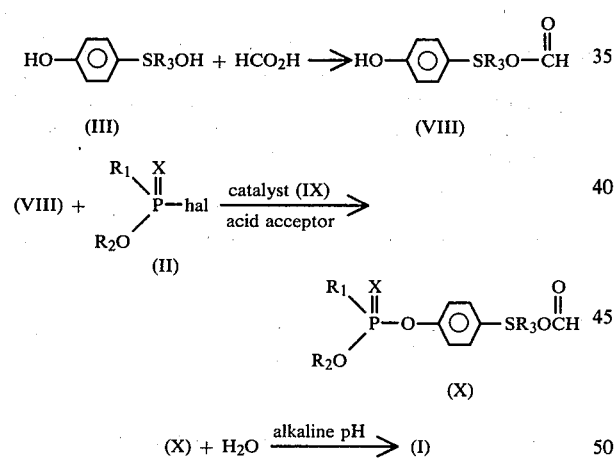

where $R_1$, $R_2$, $R_3$, X and hal have the above meaning.

The formylation of (III) may be carried out by heating under reflux a mixture of (III) in formic acid or by reacting (III) with acetic formic anhydride in an inert solvent in the presence or absence of tertiary amine catalysts. Preferably the formylation of (III) is carried out by adding acetic anhydride to a refluxing solution of (III) in formic acid. After removal of the acetic acid and excess formic acid a 99–100% yield of (VIII) is usually obtained.

Phosphorylation of (VIII) is preferably carried out in the presence of an inert solvent or diluent at a temperature between 20° and 150° C. Practically all inert organic solvents can be used for this purpose. They include, in particular, aliphatic and aromatic optionally chlorinated hydrocarbons, for example benzene, toluene, xylene, methylene chloride, chloroform, carbon tetrachloride and chlorobenzene; ethers, for example diethylether, dibutylether and dioxane; ketones, for example acetone, methyl ethyl ketone, methyl isopropyl ketone, methyl isobutyl ketone; and nitriles, for example acetonitrile and propionitrile. All customary acid binding agents may be used as acid acceptors. For example, suitable acid acceptors are alkali metal carbonates and alkali metal alcholates, such as sodium carbonate, methylate, and ethylate, and potassium carbonate, methylate and ethylate, or aliphatic aromatic or heterocyclic amines such as triethylamine, dimethylamine, dimethylbenzylamine, pyridine and the like.

In carrying out the phosphorylation of (VIII) the starting materials are in most cases employed in an equimolar ratio. An excess of one or other reactant has been found to produce no significant advantage. In general, the reaction is carried out in a solvent in the presence of an acid acceptor and optionally a catalyst at a temperature most preferably between 20° and 70° C. At the completion of the reaction thereaction mixture is poured into an organic solvent, for example, toluene. After washing with dilute hyrochloric acid, the organic phase may be dried and the solvent distilled off under reduced pressure to give (X) in 90–99% yield.

The formyl ester group of (X) is removed by mild alkaline hydrolysis. Accordingly, (X) dissolved in a water miscible solvent, and an aqueous solution of sodium or potassium carbonate, or bicarbonate, are stirred vigorously at 20° C.–60° C. Alternatively the hydrolysis of the formyl ester of (X) may be achieved by maintaining the pH of a solution of (X) in water and a water miscible solvent between pH8 and 12 by the addition of an aqueous solution of sodium or potassium hydroxide. Preferably the pH of the mixture is maintained between 11.0 and 11.5. Examples of suitable water miscible solvents for this reaction are; methanol, ethanol, dioxane, acetonitrile and the like.

When the reaction is complete the organic layer is separated, the solvent removed, the residue dissolved in an organic solvent, for example toluene, and extracted with an aqueous alkali hydroxide or carbonate solution, dried, and the solvent removed to yield 90–97% of a compound of formula (I).

In the preferred practice of the present invention a 4-dialkylamino pyridine of formula (IX):

wherein $R_4$ and $R_5$, which may be the same or different, are lower alkyl, e.g. $C_1$ to $C_4$, such as 4-dimethylamino pyridine or 4-diethylamino pyridine; or a compound of formula (XI) below wherein $R_6$ is a divalent alkylene radical of 3–5 carbon atoms, such as 4-pyrrolidino pyridine or 4-piperidino pyridine, is used to catalyse the phosphorylation of (VIII).

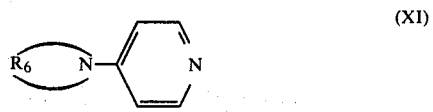

Accordingly, when the phosphorylation of (VIII) is carried out in the presence of suitable acid acceptors only 0.05 mole–0.1 mole of (IX) or (XI) per mole of (VIII) is required to increase the rate of reaction by 200 fold. The most suitable acid acceptors for use with (IX) or (XI) are tertiary amines such as trimethylamine, dimethylaniline, dimethylbenzylamine, pyridine and the like.

The following examples illustrate the invention:

EXAMPLE 1

(a) 4-(2-formyloxyethyl)thiophenol

Acetic anhydride (102 g, 1 mole) was added dropwise over 1 hour to a refluxing solution of 4-(2-hydroxyethyl)thiophenyl (170 g, 1 mole) in formic acid (95–100%, 100 mg, 2.65 mole). The mixture was heated under reflux for a further hour, then the acetic acid and excess formic acid distilled off under reduced pressure. Toluene (200 ml) was added to the residue and then distilled off under reduced pressure. The 4-(2-formyloxyethyl)thiophenol (196 g, 99%) so obtained was used below without further purification.

(b) 0,0-diethyl-0-(4-(2-formyloxyethyl)thiophenyl)phosphorothionate

To a solution of 4-(2-formyloxyethyl)thiophenol (198 g, 1 mole) prepared as described above, diethylphosphorochloridethionate (188 g, 1 mole) and 4-dimethylaminopyridine (1.83 g, 0.015 mole) in anhydrous toluene (200 ml) was added triethylamine (125 g, 1 mole) dropwise while the temperature of the reaction mixture was held at 50° C.–60° C. with external cooling. The mixture was stirred at 55°–60° C. for a further 30 min, filtered, the filtrate taken up in diethyl ether (300 ml), washed successively with dilute hydrochloric acid (2 N, 3×200 ml) and water (2×200 ml), dried over anhydrous sodium sulphate, and the solvent removed to yield a pale yellow oil (348 g, 99%).

The catalytic effect of 4-dimethylaminopyridine on the phosphorylation of 4-(2-formyloxyethyl)thiophenol was demonstrated by allowing the above reaction to proceed in the absence of the catalyst, 4-dimethylaminopyridine. No external cooling was required as the temperature of the reaction mixture only rose to 42° C. and then dropped to ambient temperature. The reaction was only substantially complete after 90 hours and when worked up as described above gave only 302 g, (86%) of 0,0-diethyl-0-(4-(2-formyloxyethyl)thiophenyl)phosphorothionate.

(c) 0,0-diethyl-0-(4-(2-hydroxyethyl)thiophenyl)phosphorothionate

An aqueous solution of potassium carbonate (152 g, 1.1 mole) in 300 ml of water) was added to a solution of 0,0-diethyl-0-(4-(2-formyloxyethyl)thiophenyl)phosphorothionate (350 g, 1 mole) prepared as described above, in ethanol (800 ml) and the mixture stirred at 20° C. overnight. The organic layer was separated, the ethanol distilled off under reduced pressure, the residue taken up in toluene (500 ml), washed successively with aqueous sodium hydroxide (10%, 2×200 ml) and water (2×200 ml), dried over anhydrous sodium sulphate and the solvent removed to yield 0,0-diethyl-0-(4-(2-hydroxyethyl)thiophenyl)phosphorothionate (306 g, 95%).

The overall yield of 0,0-diethyl-0-(4-(2-hydroxyethyl)thiophenyl)phosphorothionate based on 4-(2-hydroxyethyl)thiophenol was 94%.

EXAMPLE 2

(a) 0-Ethyl-S-n-propyl-0-(4-(2-formyloxyethyl)thiophenyl)phosphorothionthioate To a solution of 4-(2-formyloxyethyl)thiophenol (198 g, 1 mole), prepared as in example 1, 0-ethyl-S-n-propylphosphorochloridothionthiolate (218 g, 1 mole) and 4-dimethylaminopyridine (1.83 g 0.015 mole) in anhydrous methylethylketone (200 ml) was added dropwise triethylamine (125 g, 1 mole) while the temperature of the reaction mixture was held at 50°–60° C. with external cooling. The mixture was stirred at 50°–60° C. for a further 30 min, filtered, and the filtrate taken up in diethylether (300 ml), washed successively with dilute hydrochloric acid (2 N, 3×200 ml) and water (2×200 ml), dried over anhydrous sodium sulphate and the solvent removed to yield an amber oil (357 g, 94%).

(b) 0-ethyl-S-n-propyl-0-(4-(2-hydroxyethyl)thiophenyl)phosphorothionthiolate A solution of 0-ethyl-S-n-propyl-0-(4-(2-formyloxyethyl)thiophenyl)phosphorothionthioate (380 g, 1 mole) prepared as described above, in aqueous ethanol (80%, 800 ml) was maintained at pH 11.0 by the dropwise addition of aqueous sodium hydroxide (25%, 160 ml). The organic layer was separated, the ethanol removed, the residue taken up in diethyl ether (500 ml), washed with water (2×200 ml), dried over anhydrous sodium sulphate and the solvent removed to yield 0-ethyl-S-n-propyl-0-(4-(2-hydroxyethyl)thiophenyl)phosphorothionthiolate (306 g, 95%).

The overall yield of 0-ethyl-S-n-propyl-0-(4-(2-hydroxyethyl)thiophenyl)phosphorothionthiolate based on 4-(2-hydroxyethyl)thiophenol was 88%.

EXAMPLES 3 TO 5

The following compounds were prepared by analogous methods to those described in Examples 1 and 2 above.

EXAMPLE 3

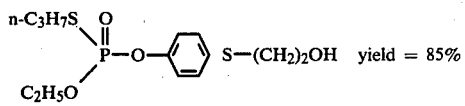

EXAMPLE 4

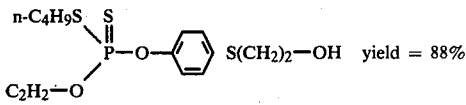

EXAMPLE 5

I claim:
1. A method for the preparation of 0-4-(hydroxyalkyl)-thiophenyl) organophosphorus esters of the formula (I):

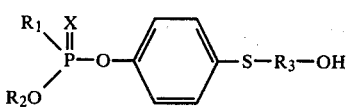 (I)

wherein: the phenolic hydroxyl group of a compound of the formula (VIII):

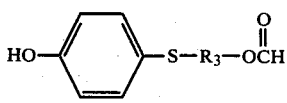 (VIII)

is phosphorylated by reaction with a compound of the formula:

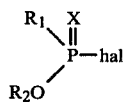 (II)

in the presence of an acid acceptor to form a compound of the formula:

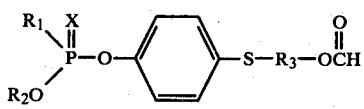 (X)

and the formyl ester group is removed from the compound of formula (X) by reaction in an alkaline solution where $R_1$ is an alkyl, alkoxy, alkylamino or alkylmercapto radical with 1-6 carbon atoms a dialkylamino radical of 2 to 6 carbon atoms or a phenyl or amino radical:

$R_2$ is an alkyl radical of 1-6 carbon atoms;
$R_3$ is a divalent alkylene radical of 1-12 carbon atoms;
X is either a sulphur or oxygen atom; and
hal is either a chlorine or bromine atom.

2. A method according to any of the preceding claims in which the phosphorylation of compound (VIII) is carried out in the presence of an inert solvent or dilutent at a temperature of between 20° and 150° C.

3. A method according to claim 1 in which the reaction involving compound (II) is carried out in an inert organic solvent.

4. A method according to claim 1 in which the reaction involving compound (II) is carried out at a temperature of from 20° to 70° C.

5. A method according to claim 1 in which the reaction involving compound (II) is carried out in the presence of a catalyst.

6. A method according to claim 5 in which the catalyst is a 4-dialkylaminopyridine of the formula (IX)

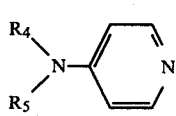 (IX)

or formula (XI)

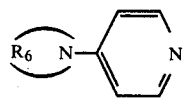 (XI)

where
$R_4$ and $R_5$ which may be the same or different, are lower alkyl radicals; and
$R_6$ is a divalent alkylene radical of 3-5 carbon atoms.

7. A method according to claim 1 in which $R_1$ is an alkoxy or alkylmercapto radical of 2-4 carbon atoms.

8. A method according to claim 7 in which $R_1$ is an ethoxy or n-propylmercapto radical.

9. A method according to claim 1 in which $R_2$ is a straight chain alkyl radical of 1 to 3 carbon atoms, and X is a sulphur atom.

10. A method according to claim 9 in which $R_2$ is an ethyl radical.

11. A method according to claim 1 in which the acid acceptor is an alkali metal carbonate or alcholate, or an aliphatic aromatic or hetercyclic amine.

12. A method according to claim 1 in which compound (X) is hydrolysed by dissolution in a water-miscible solvent and stirring with an aqueous solution of an alkaline salt at a temperature between 20° and 60° C.

13. A method according to claim 12 in which the pH of the selection is maintained between 8 and 12.

14. A method according to claim 13 in which the pH of the solution is maintained between 11.0 and 11.5.

15. A method according to claim 12 in which the solvent is methanol, ethanol, dioxane or acetonitrile.

16. A method according to claim 1 wherein the compound of formula (II) is:

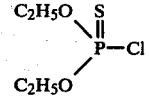

17. A method according to claim 1 wherein the compound of formula (II) is:

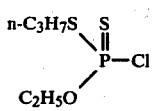

18. A method according to claim 1 wherein the compound of formula II is:

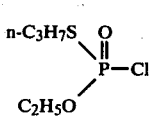

19. A method according to claim 1 wherein the compound of formula II is:

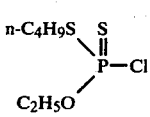

20. A method according to claim 1 wherein the compound of formula II is:

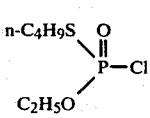

* * * * *